United States Patent [19]

Sung et al.

[11] Patent Number: 4,705,642

[45] Date of Patent: Nov. 10, 1987

[54] HAZE, OXIDATION, AND CORROSION RESISTANT DIESEL ENGINE LUBRICANT

[75] Inventors: Rodney L. Sung, Fishkill; Benjamin H. Zoleski, Beacon; Ronald L. O'Rourke, Hyde Park, all of N.Y.

[73] Assignee: Texaco Inc., White Plains, N.Y.

[21] Appl. No.: 945,599

[22] Filed: Dec. 23, 1986

Related U.S. Application Data

[63] Continuation-in-part of Ser. No. 871,990, Jun. 9, 1986, abandoned.

[51] Int. Cl.$^4$ ............... C10M 133/16; C10M 135/36
[52] U.S. Cl. .......................... 252/47.5; 252/51.5 A; 252/391; 252/392; 252/402; 252/403
[58] Field of Search ............... 252/51.5 A, 47.5, 391, 252/392, 402, 403

[56] References Cited

U.S. PATENT DOCUMENTS

| | | | |
|---|---|---|---|
| 4,326,987 | 4/1982 | Hendricks et al. | 252/51.5 R |
| 4,464,276 | 8/1984 | Sung et al. | 252/51.5 A |
| 4,536,189 | 8/1985 | Sung | 44/56 |
| 4,579,673 | 4/1986 | Piotrowski et al. | 252/51.5 A |

*Primary Examiner*—Jacqueline V. Howard
*Attorney, Agent, or Firm*—Robert A. Kulason; James J. O'Loughlin; Louis S. Sorell

[57] ABSTRACT

A haze, oxidation, and corrosion resistant diesel engine lubricant composition, particularly useful in marine and railway diesel engines, contains 0.1–5.0 weight percent of a reaction product additive. The reaction product additive is produced by first reacting substantially equimolar amounts of an anhydride compound which is either a dibasic acid anhydride or isatoic anhydride and a hydrocarbon-substituted mono primary amine or ether amine at a temperature range of 50° C.–150° C. to produce an intermediate reaction product. The intermediate reaction product is thereafter further reacted at an elevated temperature with a substantially equimolar amount of a heterocyclic azole or polyalkylene polyamine compound to form the final reaction product.

26 Claims, No Drawings

HAZE, OXIDATION, AND CORROSION RESISTANT DIESEL ENGINE LUBRICANT

CROSS-REFERENCE TO RELATED APPLICATION

This application is a continuation-in-part of applicant's copending application Ser. No. 871,990, filed June 9, 1986, now abandoned.

BACKGROUND OF THE INVENTION

1. Field of the Invention

This invention relates to a novel diesel engine crankcase lubricating composition which exhibits improved resistance to corrosion, oxidation and hazing. More particularly, this invention relates to a novel corrosion, oxidation and haze resistant diesel engine crankcase lubricating composition comprising a major amount of a hydrocarbon lubricating oil and a minor amount of the reaction product of a prescribed anhydride compound, a hydrocarbon-substituted mono primary amine or ether amine, and a nitrogen-containing heterocyclic azole or polyalkylene polyamine compound. The instant invention is particularly useful as a lubricant in large diesel engines such as marine and railway diesel engines.

As is well known to those skilled in the art, lubricating oils must be characterized by resistance to oxidation, by freedom from haze, and by rust and corrosion inhibition. Since the oils used as lubricants in the crankcases of large diesel engines, such as marine and railway diesel engines, are subject to unique conditions of operation, special attention must be directed to the potential problems which are to be encountered. These oils are typically formulated to contain anti-wear additives, oxidation inhibitors, demulsifying agents, rust-inhibitors, etc. Illustrative oils may include those of U.S. Pat. No. 4,358,386 or U.S. Pat. No. 4,375,418, inter alia.

In particular, it has been found that conventional rust-inhibited marine diesel engine crankcase lubricants tend to have haze problems caused by the presence of the rust inhibitor component. This is undesirable because it masks or interferes with determination of the presence in the lubricant of undesirable components including decomposition products, water, or solid particles.

In addition, the advent of new, more fuel efficient railway diesel engines has put a greater demand on the oxidation resistance of railway diesel lubricants. Oxidized lubricants lead to increased corrosive attack of engine metal surfaces; consequently, lubricants employed in newer railway diesel engines must be changed more frequently to prevent such corrosive attack.

It is an object of this invention to provide a novel diesel engine lubricant. It is another object to provide a novel lubricant composition, suitable for use in large marine and railway diesel engines, characterized by its resistance to oxidation, rust and corrosion inhibition, and haze-free properties. Other objects will be apparent to those skilled in the art.

2. Information Disclosure Statement

U.S. Pat. No. 4,579,673 discloses a rust-inhibited lubricant composition comprising a major amount of grease and a minor amount of a rust inhibitor additive which is the reaction product of a t-alkyl primary amine, a dialkylamine, and maleic anhydride;

Co-assigned U.S. Pat. No. 4,557,848 discloses a novel slow speed marine diesel engine crankcase lubricant characterized by decreased haze and increased corrosion inhibition, where said lubricant comprises a major amount of a mineral lubricating oil and a minor amount of a rust and haze inhibiting additive of the formula

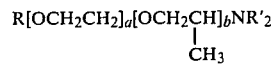

wherein R is alkyl, aralkyl, alkaryl, aryl, or cycloalkyl, R' is hydrogen or alkyl, a is 1–10, and b is 1–15;

Co-assigned U.S. Pat. No. 4,536,189 discloses a novel corrosion inhibitor which is the reaction product of maleic anhydride, a hydrocarbon-substituted mono primary amine or ether amine, and a heterocyclic compound which may be either benzotriazole or 5-amino-1,3,4,-thiadiazole-2-thiol, and motor fuels containing said novel corrosion inhibitors;

Co-assigned U.S. Pat. No. 4,464,276 describes the preparation of novel polyoxyalkylene polyamine-triazole complexes and their use in diesel lubricant compositions as antioxidants and corrosion-inhibitors;

U.S. Pat. No. 4,326,987 discloses a rust and corrosion inhibitor useful in petroleum products which is the reaction product of an alkenyl or alkyl succinic acid/anhydride and an alkyl ether diamine;

U.S. Pat. No. 4,282,008 describes a novel corrosion-inhibited fuel composition comprising gasoline, methanol or ethanol, and a minor amount of a corrosion inhibitor which is the reaction product of isatoic anhydride, a $C_3$–$C_{12}$ poly-primary amine, and an aminotriazole;

API Chemical Products Abstract, Vol. 84, para. 84-50741 (Feb. 20, 1984) describes South African Pat. No. ZA 8208904 which discloses the use of the reaction product of various aliphatic dicarboxylic compounds with various amide compounds as an additive for reducing the cloud point of middle distillates;

API Petroleum and Specialty Products Abstract, Vol. 84, para. 84-20587 (Mar. 5, 1984) describes German Pat. No. DE 3320720 which discloses the use of the reaction product of a vinyl acetate—unsaturated dicarboxylic acid compound copolymer with at least one primary amine—containing compound as an additive for corrosion inhibition and cloud point induction in middle distillates;

API Petroleum and Specialty Products Abstract, Vol. 83, para. 83-21009 (May 2, 1983) describes Eur. Pat. No. EP 71513 which discloses the use of the reaction product of a dicarboxylic acid anhydride and a primary amine-containing compound as an additive for corrosion inhibition and cloud point reduction in middle distillates; and API Primary Petroleum Products Abstract, Vol. 81, para. 81-22055 (Nov. 23, 1981) describes Eur. Pat. No. EP 34968 which discloses the use of the reaction product of maleic anhydride, an oxyalkylated alcohol and hydrocarbyl amine as a detergent and antirust additive for motor fuels.

SUMMARY OF THE INVENTION

The instant invention relates to a novel diesel engine crankcase lubricant composition which exhibits improved corrosion, oxidation, and haze resistance as compared with conventional diesel engine lubricant formulations. The novel lubricant composition of the instant invention comprises a major proportion of a hydrocarbon lubricating oil and from about 0.1 to 5.0 weight percent, preferably 0.5–2.0 weight percent (based on the lubricating oil) of the reaction product of a prescribed anhydride compound, a hydrocarbon-substituted mono primary amine or ether amine, and a nitrogen-containing heterocyclic azole or polyalkylene polyamine compound. The reaction product additive is prepared by:

(a) first reacting at a temperature ranging from 75° to 180° C. substantially equimolar amounts of an anhydride compound and a hydrocarbon-substituted mono primary amine. The anhydride reactant may be, either a dibasic acid anhydride of the formula

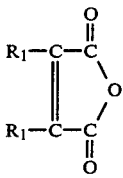

where $R_1$ is H, $CH_3$, or $C_2H_5$, or isatoic anhydride of the formula

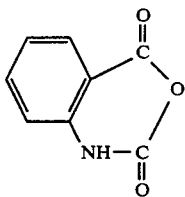

or a hydrocarbon substitued isatoic anhydride. The mono primary amine reactant may be either:

(i) a hydrocarbon-substituted mono primary amine of the formula $R-NH_2$ in which R is a monovalent straight-chained or branched-chained hydrocarbyl radical having from about 6 to about 22 carbon atoms or a hydrocarbyl aminoalkylene radical in which the hydrocarbyl group has from about 6 to about 22 carbon atoms and in which the divalent alkylene group has from about 2 to 3 carbon atoms; or (ii) a hydrocarbon-substituted mono primary ether amine of the formula

in which R is as previously described, x is an integer with a value of 0 or 1, y has a value from 0 to 10, and n is an integer from 1 to 5; and (b) thereafter further reacting at an elevated temperature said intermediate reaction product with a substantially equimolar amount of a nitrogen-containing compound which may be either:

(i) a heterocyclic azole compound selected from the group consisting of tolyltriazole, benzotriazole, aminotriazole, aminotetrazole, aminomercaptothiadiazole and benzomercaptothiazole; or (ii) a polyalkylene polyamine compound of the formula

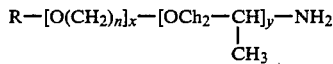

in which z is an integer from 1 to 5.

DETAILED EMBODIMENTS OF THE INVENTION

The lubricants set forth by the instant invention include lubricating oils which are employed in large diesel engines, particularly in the crankcases of large diesel engines such as are found in marine service, and in large railway diesel engine.

The novel corrosion, oxidation, and haze resistant diesel engine lubricating oil of the instant invention comprises a major amount of a base hydrocarbon lubricating oil and from 0.1 to 5.0 weight percent, preferably 0.5 to 2.0 weight percent of an additive which is the reaction product of a prescribed anhydride compound which is either a dibasic acid anhydride or isatoic anhydride, a hydrocarbon-substituted mono primary amine or ether amine, and a nitrogen-containing heterocyclic azole or polyalkylene polyamine compound.

The base hydrocarbon oil which may be employed to prepare the lubricating oil composition of the invention includes naphthenic base, paraffinic base and mixed base mineral oils, lubricating oil derived from coal products and synthetic oils, e.g. alkylene polymers such as polypropylene and polyisobutylene of a molecular weight of between about 250 and 2500. In the case of marine diesel engine lubricants, the preferred lubricant is typically a hydrocarbon lubricating oil having a Total Base Number (TBN) of 3–8, say 6 made up for example by blending a paraffinic Solvent Neutral Oil (SNO-20) having a VI of ca 92 and a viscosity of 47–53 CSt at 40° C. and 6.65–7.15 at 100° C. with a paraffinic Solvent Neutral Oil (SNO-50) having a VI of ca 93 and a viscosity of 158–180 CSt at 40° C. and 15.3–16.4 at 100° C. In the case of railway diesel engine lubricants, the preferred lubricant is typically a mixture of a paraffinic mineral oil of a viscosity of 5.5–10.0, say 8.5 CSt at 100° C., a paraffinic mineral oil of a viscosity of 8.0–15.0, say 14.5 CSt at 100° C., and a naphthenic pale oil of a viscosity of 8.0–15.0, say 14.2 CSt at 100° C.

Typically, the lubricant composition of the instant invention may contain minor amounts of additional additives. Table I sets forth illustrative additives which may be employed in admixture with the instant invention when it is used as a marine diesel engine lubricant.

TABLE I

| Additive Function | Broad Range (wt. %) | Illustrative Additive |
|---|---|---|
| Anti-wear Agent | 0.1–1 | Zinc dialkyl dithiophosphate |
| Oxidation Inhibitor | 0.1–1 | alkylated diphenyl amine |
| Demulsifying Agents | 50–200 ppm | dimethyl polysiloxane (a silicone) |
| Detergent | 1–5 | Overbased sulfurized calcium alkylphenolate |
| Anti-Rust Agent | 0.1–5 | Ethoxylated nonyl phenol |

When the lubricant composition of the instant invention is used as a railway diesel engine lubricant, additional additives or additive packages may also be employed. An illustrative example of an additive concentrate package (commercially available as ORONITE OLOA 2939) which may be employed in admixture with the lubricant composition of the instant invention is set forth in Table II.

TABLE II

| Additive | Typical Concentration (wt. %)* |
| --- | --- |
| Overbased mixed calcium petroleum sulfonate/phenolate | 45 |
| Polyisobutenyl succinimide/amide | 10 |
| Polyisobutylene | 1.5 |
| Paraffinic Mineral Oil | 43 |
| Chloroparaffin | 0.5 |

*Wt. % concentration based on total weight of additive concentrate package.

The reaction product additive component of the lubricant composition of the instant invention is prepared by first reacting substantially equimolar amounts of an anhydride compound which may be either a dibasic acid anhydride or isatoic anhydride, and a hydrocarbon-substituted mono primary amine or ether amine to produce an intermediate reaction product. This intermediate product is thereafter reacted with a substantially equimolar amount of a nitrogen-containing heterocyclic azole or polyalkylene polyamine compound to produce the prescribed reaction product additive.

The isatoic anhydride reactant which may be employed to prepare the reaction product is of the formula:

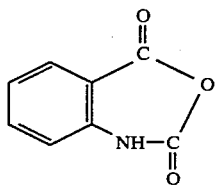

The above reactant may bear inert substituents (which do not interfere with the reaction) on the nitrogen atom or on the ring. Typical of these may be alkyl, aralkyl, alkaryl, aryl, or cycloalkyl hydrocarbon substituents. The ring may also bear other inert substituents typified by alkoxy, aryloxy, etc.

The dibasic acid anhydride reactant which may be employed to prepare the reaction product is of the formula

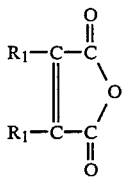

where $R_1$ is H, $CH_3$, or $C_2H_5$. Accordingly, dibasic acid anhydrides suitable for use include maleic anhydride; alpha-methyl maleic anhydride; alpha-ethyl maleic anhydride; and alpha, beta-dimethyl maleic anhydride. The preferred dibasic acid anhydride for use in maleic anhydride.

The amine reactant which is employed to prepare the prescribed reaction product is of one of two types. One type is represented by the formula

in which R is a monovalent straight-chained or branched-chained saturated or unsaturated hydrocarbyl radical of from about 6 to about 22 carbon atoms or a hydrocarbyl amino alkylene radical in which the hydrocarbyl group has from about 6 to about 22 carbon atoms and in which the divalent alkylene group has from about 2 to 3 carbon atoms.

In one type of suitable hydrocarbon-substituted mono primary amine, R is an aliphatic radical having from 10 to 18 carbon atoms. Examples of amines of this type are those sold under the ARMEEN trademark by the Armak Co., and they include ARMEEN C (cocoamine) having a typical chain length distribution ranging from $C_8$ to $C_{18}$ with 51% being saturated $C_{12}$ alkyl groups; ARMEEN OL (oleylamine) having a typical chain length distribution ranging from $C_{12}$ to $C_{18}$ with 76% being oleyl; and ARMEEN T (tallowamine) having a typical chain length distribution ranging from $C_{14}$ to $C_{18}$ with 29% being unsaturated $C_{16}$ groups.

Examples of preferred branched-chained mono primary amines include single isomer t-alkyl primary amines such as t-octylamine. Other preferred branched-chained primary amines are those sold by the Rohm & Haas Co. under the PRIMENE 81-R and PRIMENE JM-T trademarks. PRIMENE 81-R is a mixture of t-mono primary amines containing different isomers which typically range from $t-C_{12}H_{25}NH_2$ to $t-C_{14}H_{29}NH_2$. PRIMENE JM-T is a mixture of t-mono primary amines containing different isomers which typically range from $t-C_{18}H_{37}NH_2$ to $t-C_{22}H_{45}NH_2$.

In still another type of suitable hydrocarbon-substituted mono primary amine, R is a hydrocarbyl aminoalkylene radical. Preferably, the hydrocarbyl group comprises an aliphatic group having from 10 to 18 carbon atoms, and the divalent alkylene group comprises 3 carbon atoms. Amines of this type are sold under the DUOMEEN trademark by the Armak Co., and they include DUOMEEN C which is the hydrogenated cocoamine adduct of acrylonitrile; DUOMEEN T which is the hydrogenated adduct of tallowamine and acrylonitrile; and DUOMEEN O which is the hydrogenated adduct of an amine and acrylonitrile, wherein the amine is an unsaturated primary amine having about 18 carbon atoms.

The other amine reactant is a hydrocarbon-substituted mono primary ether amine which is represented by the formula

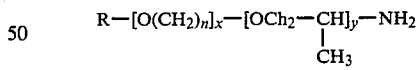

in which R is as previously described, x is an integer with a value of 0 or 1, y has a value from 0 to 10, and n is an integer from 1 to 5. Preferably, R is an aliphatic radical having from 10 to 18 carbon atoms, when y is 0, x is 1, and n is 2 to 3, and when x is 0, y has a value of 1 to 5. More preferably, R is an aliphatic radical having from 10 to 13 carbon atoms, when y is 0, x is 1 and n is 3, and when x is 0, y is 2.

Suitable hydrocarbon-substituted mono primary ether amines where y is 0 are sold by Armak Co. under the ARMEEN EA-13 trademark which has a typical chain length distribution of $C_{13}$ carbon atoms with n equal to 3, and sold by the Tomah Chemical Co. under the TOMAH PA-17 trademark which has a chain length distribution of $C_{10}$ to $C_{13}$ with n equal to 3. Suitable hydrocarbon-substituted mono primary ether amines where x is 0 are sold by the Texaco Chemical Co. under the JEFFAMINE M-300 trademark which has a typical chain length distribution ranging from $C_{10}$ to $C_{12}$ and with y equal to 2.

To produce the final reaction product additive, the intermediate reaction product is thereafter reacted at elevated temperatures with a substantially equimolar amount of a nitrogen-containing compound which may be either:

(i) a heterocyclic azole compound selected from the group consisting of tolyltriazole (hereinafter referred to as TTZ), benzotriazole (hereinafter referred to as BTZ), aminotriazole (hereinafter referred to as ATZ), aminotetrazole (hereinafter referred to as ATTZ), aminomercaptothiadiazole (hereinafter referred to as AMTZ), and benzomercaptothiazole (hereinafter referred to as BMTZ); or (ii) a polyalkylene polyamine compound of the formula

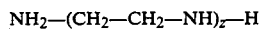

in which z is an integer from 1 to 5, preferably 1 to 3.

If an aminotriazole reactant is employed, it preferably will be a 3-, 4-, or 5-aminotriazole (hereinafter referred to as 3-ATZ, 4-ATZ, or 5-ATZ, respectively), including those bearing inert substituents, typified by hydrocarbon or alkoxy groups, which do not react in the instant invention. If an aminotetrazole reactant is employed, it preferably will be a 4- or 5-aminotetrazole (hereinafter referred to as 4-ATTZ or 5-ATTZ, respectively), again including those bearing inert substituents, typified by hydrocarbon or alkoxy groups which do not react in the instant invention. If an aminomercaptothiadiazole reactant is employed, it preferably will be a 5-aminomercaptothiadiazole, most preferably 5-amino-2-mercapto-1,3,4 thiadiazole. If a polyalkylene polyamine reactant is employed, preferred polyalkylene polyamine compounds for use include ethylenediamine (hereinafter referred to as EDA), diethylene triamine (hereinafter referred to as DETA), and triethylene tetramine (hereinafter referred to as TETTA).

In the best mode of preparing the reaction product additive of the instant invention, the prescribed anhydride reactant is dissolved in a solvent such as xylene, hexene, or dimethyl formamide, and heated to about 60° C. Where the prescribed anhydride reactant is dibasic acid anhydride, the preferred solvent for use is xylene. Where the prescribed anhydride reactant is isatoic anhydride, the preferred solvent for use is dimethyl formamide. An amount of the hydrocarbon-substituted mono primary amine or mono primary ether amine is then added to the solution such that substantially equimolar amounts of anhydride and amine reactants are present, and the resultant mixture if heated for 2 to 4 hours at 50° to 150° C., thereby forming the intermediate reaction product. To the mixture containing the intermediate product an equimolar amount of a nitrogen-containing heterocyclic compound selected from the group consisting of TTZ, BTZ, 3-ATZ, 4-ATZ, 5-ATZ, 4-ATTZ, 5-ATTZ, AMTZ, and BMTZ, or a polyalkylene polyamine such as EDA, DETA, or TETTA is added and the entire mixture is then heated to effect the reaction. In general, this is done by heating the mixture to the reflux temperature and maintaining it under these conditions for the required length of time. The reaction can generally be completed in from about 0.1 to 10 hours, although longer time may be required for large quantities. After the water is removed from the sysem, the product is filtered and stripped under a vacuum.

The following examples illustrate the preferred method of preparing the reaction product additive of the instant invention. It will be understood that the following examples are merely illustrative, and are not meant to limit the invention in any way. In the examples, all parts are parts by weight unless otherwise specified.

EXAMPLE 1

Preparation of Maleic Anhydride, Hydrocarbon-Substituted Mono Primary Ether Amine and 5-ATTZ Reaction Product 98 parts of maleic anhydride dissolved in 172 parts of xylene were heated at 60° C. 284 parts of decylidioxyisopropylamine (JEFFAMINE M-300) were than added, and this mixture was reacted at 100° C. for 2 hours and then allowed to cool to room temperature. 83 parts of 5-ATTZ were then added to the mixture, and the entire mixture was reacted at the reflux temperature of xylene. After all the water of reaction was distilled off, the heating was stopped and the reaction product was filtered and stripped of remaining solvent under a vacuum.

EXAMPLE 2A

Preparation of Maleic Anhydride, Hydrocarbon-Substituted Mono Primary Ether Amine and 5-ATTZ Reaction Product 98 parts of maleic anhydride dissolved in 373 parts of xylene were heated at 60° C. 275 parts of tridecoxypropyleneamine (ARMEEN EA-13) were than added and this mixture was reacted at 100° C. for 2 hours and then allowed to cool to room temperature. 83 parts of 5-ATTZ were then added to the mixture, and the entire mixture was then reacted at the reflux temperature of xylene. After the water of reaction was distilled off, the heating was stopped and the reaction product was filtered and stripped of remaining solvent under a vacuum.

EXAMPLE 2B

Preparation of Maleic Anhydride, Hydrocarbon-Substituted Mono Primary Ether Amine and 5-ATTZ Reaction Product 98 parts of maleic anhydride dissolved in 373 parts of xylene were mixed with 275 parts of ARMEEN EA-13. The mixture was heated for 2 hours at 100° C. and then allowed to cool to room temperature. To 75 parts of the above intermediate reaction product, 21 parts of 5-ATTZ and 175 parts of xylene were added, and this mixture was then reacted at the reflux temperature of xylene. After the water of reaction was distilled off, the heating was stopped and the reaction product was filtered and stripped of remaining solvent under a vacuum.

EXAMPLE 3

Preparation of a Maleic Anhydride, Hydrocarbon-Substituted Mono Primary Ether Amine and 5-ATTZ Reaction Product 98 parts of maleic anhydride dissolved in 200 parts of xylene were heated to 60° C. 340 parts of decoxypropyleneamine (TOMAH PA-17) were then added, and this mixture was reacted at 100° C. for 2 hours and then allowed to cool to room temperature. To one-half of the above intermediate reaction product mixture were added 33 parts of 5-ATTZ, and the entire mixture was then reacted at the reflux temperature of xylene. After all the water of reaction was distilled off, the heating was stopped and the reaction product was filtered and stripped of remaining solvent under a vacuum.

EXAMPLE 4

Preparation of Maleic Anhydride, Hydrocarbon-Substituted Mono Primary Ether Amine and AMTZ Reaction Product 49 parts of maleic anhydride dissolved in 86 parts of xylene were heated to 60° C. 142 parts of decyldioxyisopropylamine (JEFFAMINE M-300) were then added, and this mixture was reacted at 100° C. for 2 hours, then allowed to cool to room temperature. 33 parts of AMTZ were then added to the mixture, and the entire mixture was reacted at the reflux temperature of xylene. After all the water of reaction was distilled off, the heating was stopped and the reaction product was filtered and stripped of remaining solvent under a vacuum.

EXAMPLE 5

Preparation of Maleic Anhydride, Hydrocarbon-Substituted Mono Primary Ether Amine and AMTZ Reaction Product 98 parts of maleic anhydride dissolved in 373 parts of xylene were heated to 60° C. 275 parts of tridecoxypropyleneamine (ARMEEN EA-13) were then added, and this mixture was reacted at 100° C. for 2 hours, then cooled to room temperature. To 75 parts of the intermediate reaction product were added 26.4 parts of AMTZ and 171 parts of xylene, and the entire mixture was then reacted at the reflux temperature of xylene. After all the water of reaction was distilled off, the heating was stopped and the reaction product was filtered and stripped of remaining solvent under a vacuum.

EXAMPLE 6

Preparation of Maleic Anhydride, Hydrocarbon-Substituted Mono Primary Ether Amine and AMTZ Reaction Product 98 parts of maleic anhydride dissolved in 200 parts of xylene were heated to 60° C. 340 parts of decoxypropyleneamine (TOMAH PA-17) were than added and this mixture was reacted at 100° C. for 2 hours, then cooled to room temperature. Half of the intermediate reaction product was removed, and to it was added 33 parts of AMTZ. The entire mixture was then reacted at the reflux temperature of xylene. After all the water of reaction was distilled off, the heating was stopped and the reaction product was filtered and stripped of remaining solvent under a vacuum.

EXAMPLE 7

Preparation of Maleic Anhydride, Hydrocarbon-Substituted Mono Primary Amine and AMTZ Reaction Product 25 parts of maleic anhydride dissolved in 200 parts of xylene were heated to 60° C. 66 parts of oleylamine (ARMEEN OL) were then added, and this mixture was reacted at 100° C. for 2 hours, then cooled to room temperature. Thereafter, 33 parts of AMTZ were added to the mixture, and the entire mixture was reacted at the reflux temperature of xylene. After all the water of reaction was distilled off, the heating was stopped and the reaction product was filtered and stripped of remaining solvent under a vacuum.

EXAMPLE 8A

Preparation of Maleic Anhydride, Hydrocarbon-Substituted Mono Primary Ether Amine and BTZ Reaction Product 98 parts of maleic anhydride dissolved in 388 parts of xylene were heated to 60° C. 289.5 parts of decyldioxyisopropylamine (JEFFAMINE M-300) were than added, and this mixture was reacted at 100° C. for 2 hours, then cooled to room temperature. 156 parts of the above mixture were removed and added to 24 parts of BTZ and 94 parts of xylene. This mixture was then reacted at the reflux temperature of xylene. After all the water of reaction was distilled off, the heating was stopped and the reaction product was filtered and stripped of remaining solvent under a vacuum.

EXAMPLE 8B

Preparation of Maleic Anhydride, Hydrocarbon-Substituted Mono Primary Ether Amine and BTZ Reaction Product 98 parts of maleic anhydride dissolved in 388 parts of xylene were heated to 60° C. Thereafter, 373 parts of JEFFAMINE M-300 were added, and the mixture was heated at 100° C. for 2 hours. To 150 parts of the above intermediate reaction product, 24 parts BTZ in 94 parts xylene were added, and this mixture was then reacted at the reflux temperature of xylene. After the water of reaction was distilled off, the heating was stopped and the reaction product was filtered and stripped of remaining solvent under a vacuum.

EXAMPLE 9

Preparation of Maleic Anhydride, Hydrocarbon-Substituted Mono Primary Ether Amine and BTZ Reaction Product 98 parts of maleic anhydride dissolved in 438 parts of xylene were heated to 60° C. 340 parts of decoxypropyleneamine (TOMAH PA-17) were then added, and this mixture was reacted at 100° C. for 2 hours, then cooled to room temperature. 59.5 parts of BTZ were then added to the mixture, and the entire mixture was reacted at the reflux temperature of xylene. After all the water of reaction was distilled off, the heating was stopped and the reaction product was filtered and stripped of remaining solvent under a vacuum.

EXAMPLE 10

Preparation of Maleic Anhydride, Hydrocarbon-Substituted Mono Primary Ether Amine and BTZ Reaction Product 98 parts of maleic anhydride dissolved in 373 parts of xylene were heated to 60° C. 275 parts of tridecoxypropyleneamine (ARMEEN EA-13) were then added and this mixture was reacted at 100° C. for 2 hours, then cooled to room temperature. To 75 parts of the intermediate product were added 24 parts of BTZ. The entire mixture was then reacted at the reflux temperature of xylene. After all the water of reaction was distilled off, the heating was stopped and the reaction product was filtered and stripped of remaining solvent under a vacuum.

EXAMPLE 11

Preparation of Maleic Anhydride, Hydrocarbon-Substituted Mono Primary Ether Amine and DETA Reaction Product 9.8 parts of maleic anhydride dissolved in 46 parts of xylene were heated to 60° C. 27.5 parts of tridecoxy-propyleneamine (ARMEEN EA-13) were than added and this mixture was reacted at 100° C. for 2 hours, then cooled to room temperature. 10.3 parts of DETA were then added to the mixture, and the entire mixture was reacted at the reflux temperature of xylene. After all the water of reaction was distilled off, the heating was stopped and the reaction product was filtered and stripped of remaining solvent under a vacuum.

EXAMPLE 12

Preparation of Maleic Anhydride, Hydrocarbon-Substituted Mono Primary Ether Amine and DETA Reaction Product 98 parts of maleic anhydride dissolved in 200 parts of xylene were heated to 60° C. 340 parts of decoxy-propyleneamine (TOMAH PA-17) were than added and this mixture was reacted at 100° C. for 2 hours, then cooled to room temperature. 183 parts of DETA were then added to the mixture, and the entire mixture was reacted at the reflux temperature of xylene. After all the water of reaction was distilled off, the heating was stopped and the reaction product was filtered and stripped of remaining solvent under a vacuum.

EXAMPLE 13

Preparation of Maleic Anhydride, Hydrocarbon-Substituted Mono Primary Ether Amine and 5-ATZ Reaction Product 98 parts of maleic anhydride dissolved in 373 parts of xylene were heated to 60° C. 275 parts of ARMEEN EA-13 were then added, and this mixture was reacted at 100° C. for 2 hours, then cooled to room temperature. To 75 parts of the intermediate reaction product, 17 parts of 5-ATZ and 173 parts of xylene were added. The mixture was then reacted at the reflux temperature of xylene. After all the water of reaction was distilled off, the heating was stopped and the reaction product was filtered and stripped of remaining solvent under a vacuum.

EXAMPLE 14

Preparation of Isatoic Anhydride, T-Alkyl Primary Amine and BTZ Reaction Product 82 parts of isatoic anhydride dissolved in 200 parts of dimethyl formamide were heated to 60° C. 62.5 parts of PRIMENE JMT were then added, and this mixture was heated to its reflux temperature and refluxed for 24 hours, then cooled to room temperature. 59.5 parts of BTZ were then added to the mixture, and the entire mixture was reacted at the reflux temperature of dimethyl formamide. After all the water of reaction was distilled off, the heating was stopped and the reaction product was filtered and stripped of remaining solvent under a vacuum.

The above-described reaction products may be added to the base lubricating oil in minor, effective, corrosion inhibiting amounts of about 0.1-5.0 wt. %. Lesser quantities may be employed, but the degree of improvement so obtained may be lessened thereby. Larger amounts may be employed, but no significant additional improvement is thereby attained. Preferably the effective amount is about 0.5-2.0 wt. %, say about 1.0 wt. % based on the lubricating oil. The reaction product compound may be added separately or as a component of an additive package which contains other additives.

Presence of the above-described reaction product compounds in a diesel engine lubricating oil such as a marine diesel engine lubricant is found to be particularly advantageous in several respects, including the minimization of haze in the oil. Haze may be determined by visual inspection or by colorimetric techniques. In the Lumetron Turbidity Test, a standard light beam is passed through a sample to be tested and the amount of light which passes through the sample is measured by a photo cell. Results are obtained as % readings. A high reading of say 30 or above indicates substantial haze which is unsatisfactory. A low reading of 10-15 or below indicates a low level of haze which is satisfactory. As measured by the Lumetron Turbidity Test, practice of this invention may decrease the haze from an unsatisfactory reading of say 40-60 to a satisfactory level of say 5-10 in the case of marine diesel crankcase oil.

Presence of the reaction product compound in a marine crankcase lubricating oil will also permit attainment of satisfactory rust inhibition as measured by the Salt Water Rust Test ASTM-D-655. Oils which fail the Salt Water Rust Test may be improved by use of the instant additive to the point at which they pass the test.

It is highly desirable to obtain a corrosion and rust inhibitor which does not contribute haze to the lubricant, because haze is generally regarded as an index of lubricant deterioration. Practice of this invention will be apparent to those skilled in the art from inspection of the following examples.

EXAMPLE 15

In this control example, a standard marine diesel engine crankcase lubricating oil was formulated containing the following components:

| | Component | wt. % |
|---|---|---|
| (i) | SNO-20 G, a paraffinic Solvent Neutral Oil having a viscosity at 100° C. of 6.65-7.15 SUS and a VI of ca 92 | 39.30 |
| (ii) | SNO-50, a paraffinic Solvent Neutral Oil having a viscosity at 100° C. of 15.3-16.4 SUS and a VI of ca 93 | 55.80 |
| (iii) | ORONITE 218A brand of overbased sulfurized calcium alkylphenolate having a TBN of 147 (detergent) | 3.60 |
| (iv) | Zinc dialkyl dithiophosphate - the zinc salt of the reaction product of $P_2S_5$ and mixed $C_2$-$C_4$ alcohol (anti-wear and anti-oxidant) | 0.65 |
| (v) | VANLUBE NA brand of Dinonyl phenyl amine (anti-oxidant) | 0.30 |
| (vi) | SURFONIC N-60 Brand of ethoxylated (6) nonyl phenol (anti-rust agent) | 0.35 |
| (vii) | Dimethyl polysiloxane (silicone) (anti-foamant) | 150 ppm |

This formulation as so made up (which is representative of prior art marine diesel engine crankcase lubricating oils) was found to have Lumetron Turbidity of 55. This is unsatisfactory. If additional quantities of the Surfonic N-60 anti-rust additive were added, the haze would be worse, i.e. the Lumetron Turbidity would increase.

EXAMPLE 16

A control formulation was made up identical to that of Example 15 except that it did not contain the SURFONIC N-60 brand of rust inhibitor. The Lumetron Turbidity test showed a satisfactory rating of 9; but the Salt Water Rust Test yielded a "Fail" rating.

EXAMPLE 17

To the base lubricant formulation of Example 16 was added 1.0 wt. % of the reaction product of Example I. The Lumetron Turbidity Test showed a satisfactory rating of 3.0, and the ASTM Salt Water Rust Test yielded a "Pass" rating.

EXAMPLE 18

To the base lubricant formulation of Example 16 was added 1.0 wt. % of the reaction product of Example II. The Lumetron Turbidity Test showed a satisfactory rating of 8.0, and the ASTM Salt Water Rust Test yielded a "Pass" rating.

EXAMPLE 19

To the base lubricant formulation of Example 16 was added 1.0 wt. % of the reaction product of Example 6. The Lumetron Turbidity Test showed a satisfactory rating of 18, and the ASTM Salt Water Rust Test yielded a "Pass" rating.

EXAMPLE 20

To the base lubricant formulation of Example 16 was added 1.0 wt. % of the reaction product of Example 7. The Lumetron Turbidity Test showed a satisfactory rating of 6.0, and the ASTM Salt Water Rust Test yielded a "Pass" rating.

EXAMPLE 21

To the base lubricant formulation of Example 16 was added 1.0 wt. % of the reaction point of Example 8. The Lumetron Turbidity Test showed a satisfactory rating of 8.0, and the ASTM Salt Water Rust Test yielded a "Pass" rating.

EXAMPLE 22

To the base lubricant formulation of Example 16 was added 1.0 wt. % of the reaction product of Example 9. The Lumetron Turbidity Test showed a satisfactory rating of 5.0, and the ASTM Salt Water Rust Test yielded a "Pass" rating.

EXAMPLE 23

To the base lubricant formulation of Example 16 was added 1.0 wt. % of the reaction product of Example 10. The Lumetron Turbidity Test showed a satisfactory rating of 5.0, and the ASTM Salt Water Rust Test yielded a "Pass" rating.

EXAMPLE 24

To the base lubricant formulation of Example 16 was added 1.0 wt. % of the reaction product of Example 11. The Lumetron Turbidity Test showed a satisfactory rating of 2.5, and the ASTM Salt Water Rust Test yielded a "Pass" rating.

EXAMPLE 25

To the base lubricant formulation of Example 16 was added 1.0 wt. % of the reaction product of Example 12. The Lumetron Turbidity Test showed a satisfactory rating of 5.5, and the ASTM Salt Water Rust Test yielded a "Pass" rating.

As the above Examples 17-25 demonstrate, the compositions of the instant invention formulated for use as marine diesel engine lubricants exhibit improved rust and haze inhibition in comparison with Example 15, which contained a conventional rust inhibitor but exhibited unsatisfactory hazing, and Example 16, which exhibited a satisfactory haze rating but lacked any rust inhibitor.

Presence of the above-described reaction product compound in a diesel engine lubricating oil such as a railway diesel engine lubricant is found to be particularly advantageous in controlling the degradation of the lubricant under typical engine operating conditions. Degradation of the lubricant often leads to higher acid concentrations within the lubricant, which in turn leads to corrosive attack of metallic engine surfaces.

The ARCO Railroad Oil Oxidation Test (ARCO Test) was employed to determine the degradation characteristics of lubricant compositions of the instant invention. The ARCO Test is intended for the determination of the oxidation and corrosion characteristics of diesel engine lubricants, is especially useful as a screening test for railway diesel engine lubricants, and correlates well with results obtained from the 250-hour EMD 2-567 engine test.

The ARCO Test method involves bubbling oxygen at a rate of 5 liters/hr. through 300 gm of test oil held at 300° F. in the presence of three metal coupons, one each made of copper, lead, and steel. At the end of the Test, the total weight change of the coupons is measured, thereby determining the oxidation characteristics of the test oil vis-a-vis the metal coupons. The detailed procedure of the ARCO Test is set forth below.

Three square metal coupons are cut from metal sheets, as follows:

| COUPON MATERIAL | DIMENSIONS mm × mm × mm | WEIGHT. gm APPROX. |
|---|---|---|
| Copper Electrolytic Copper | 25.4 × 25.4 × 3.12 | 17-18 |
| Steel Mild Carbon Steel | 25.4 × 25.4 × 3.07 | 15-16 |
| Lead Chemical Grade Lead | 25.4 × 25.4 × 1.52 | 11-12 |

Two 2.38-mm holes are drilled in each coupon, and the coupons are polished with fine emery cloth and steel wool to obtain a clean, smooth surface, then washed with acetone, dried, and tared. Using clean cotton cord, the coupons are tied together as a hollow prism which stands in an oxidation cell assembly. The oxidation cell includes a test tube, an oxygen inlet tube and a condenser, and is the same cell as used in ASTM Method D-943 "Oxidation Characteristics of Inhibited Steam Turbine Oils" except that no cooling water is used for the condenser.

After placing the coupons into the oxidation cell, the cell is filled with 300 gm of the oil to be tested. The cell is then placed in an oil bath which has been previously adjusted to a temperature of 300±2° F., and heated for 48 hours. Oxygen at a flow rate of 5±0.2 liters/hr. is constantly contacted with the test oil. At the end of 48 hours, the oxygen flow is stopped, and the cell is taken out of the bath and allowed to cool to room temperature.

The coupons are then removed from the cell, washed with a 50/50 blend of toluene and acetone, and allowed to dry. The coupons are thereafter weighed to determine weight changes due to oil oxidation of the metal surfaces. The weight changes of the coupons are reported as the total weight loss of all three coupons. The larger the total weight loss of the coupons, the more likely it is that the test oil will oxidize and lead to corrosive attack of engine metal surfaces. In addition, the viscosities of the test oil before and after the Test are measured to determine the effect of oxidation on oil viscosity. The greater the percentage increase in viscosity due to oxidation, the greater the degree of oil degradation which has occurred.

The following examples and ARCO Test results further illustrate the superiority of the instant invention as a diesel engine lubricant, particularly as a railway diesel engine lubricant.

EXAMPLE 26

In this control example, a standard railway diesel engine lubricant was formulated containing the following components:

| | Component | wt. % |
|---|---|---|
| (i) | Paraffinic mineral oil of viscosity 8.46 CSt at 100° C. | 19.12 |
| (ii) | Paraffinic mineral oil of viscosity 14.5 CSt at 100° C. | 22.48 |
| (iii) | Naphthenic pale oil of viscosity 14.2 CSt at 100° C. | 43.76 |
| (iv) | ORONITE OLOA 2939 brand additive package* | 14.64 |

*See Table II

This formulation is representative of conventional railway diesel engine crankcase lubricants. It was tested via the ARCO Test and found to have a total coupon weight loss of 0.2208 gm and a viscosity increase of 14.7%.

EXAMPLE 27

A lubricant formulation was made up containing 99 wt. % of the base lubricant of Example 26 and 1.0 wt. % of the reaction product of Example 2B. This formulation is representative of lubricant formulations of the instant invention. It was tested via the ARCO Test and found to have a total coupon weight loss of 0.0670 gm and a viscosity increase of 12.0%.

EXAMPLE 28

A lubricant formulation was made up containing 99 wt. % of the base lubricant of Example 26 and 1.0 wt. % of the reaction product of Example 8B. This formulation is representative of lubricant formulations of the instant invention. It was tested via the ARCO Test and found to have a total coupon weight loss of 0.0850 gm and a viscosity increase of 12.5%.

EXAMPLE 29

A lubricant formulation was made up containing 99 wt. % of the base lubricant of Example 26 and 1.0 wt. % of the reaction product of Example 9. This formulation is representative of lubricant formulations of the instant invention. It was tested via the ARCO Test and found to have a total coupon weight loss of 0.0615 gm and a viscosity increase of 11.1%.

EXAMPLE 30

A lubricant formulation was made up containing 99 wt. % of the base lubricant of Example 26 and 1.0 wt. % of the reaction product of Example 10. This formulation is representative of lubricant formulations of the instant invention. It was tested via the ARCO Test and found to have a total coupon weight loss of 0.0729 gm and a viscosity increase of 12.2%.

EXAMPLE 31

A lubricant formulation was made up containing 99 wt. % of the base lubricant of Example 26 and 1.0 wt. % of the reaction product of Example 13. This formulation is representative of lubricant formulations of the instant invention. It was tested via the ARCO Test and found to have a total coupon weight loss of 0.0351 gm and a viscosity increase of 10.1%.

EXAMPLE 32

A lubricant formulation was made up containing 99 wt. % of the base lubricant of Example 26 and 1.0 wt. % of the reaction product of Example 14. This formulation is representative of lubricant formulations of the instant invention. It was tested via the ARCO Test and found to have a total coupon weight loss of 0.0841 gm and a viscosity increase of 12.3%.

Table III below summarizes the results obtained from the ARCO Test for lubricant compositions Examples 26–32.

TABLE III

| Example Additive | Reaction Product | Total Coupon Wt. Loss (gm) | Visc. Increase (%) |
|---|---|---|---|
| 26 | None | 0.2208 | 14.7 |
| 27 | Maleic Anhydride, ARMEEN EA-13, and 5-ATTZ (Example 2B) | 0.0670 | 12.0 |
| 28 | Maleic Anhydride, JEFFAMINE M-300, and BTZ (Example 8B) | 0.0850 | 12.5 |
| 29 | Maleic Anhydride, TOMAH PA-17, and BTZ (Example 9) | 0.0615 | 11.1 |
| 30 | Maleic Anhydride, ARMEEN EA-13, and BTZ (Example 10) | 0.0729 | 12.2 |
| 31 | Maleic Anhydride, ARMEEN EA-13, and 5-ATZ (Example 13) | 0.0351 | 10.1 |
| 32 | Isatoic Anhydride, PRIMENE JMT, and BTZ (Example 14) | 0.0841 | 12.3 |

As demonstrated by Table III, the compositions of the instant invention (Examples 27–32) formulated for use as railway diesel engine lubricants exhibited less degradation after exposure to the test conditions of the ARCO Test than the conventional railway diesel engine lubricant of Example 26. All of the Examples of the instant invention demonstrated both lower total coupon weight loss (hence less corrosive attack of metal surfaces) and less viscosity increase (hence less oxidation) than Example 26.

Although this invention has been illustrated by reference to specific embodiments, it will be apparent to those skilled in the art that various changes and modifications may be made which clearly fall within the scope of this invention.

The invention claimed is:

1. A lubricating oil composition suitable for use in a diesel engine, comprising a major proportion of a hydrocarbon lubricating oil and from about 0.1 to 5.0 weight percent of a reaction product prepared by:
(a) first reacting at a temperature ranging from 50° to 150° C. substantially equimolar amounts of an anhydride compound and a hydrocarbon-substituted mono primary amine to produce an intermediate reaction product, where said anhydride reactant is either a dibasic acid anhydride of the formula

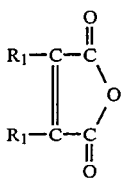

where $R_1$ is H, $CH_3$, or $C_2H_5$, or isatoic anhydride of the formula

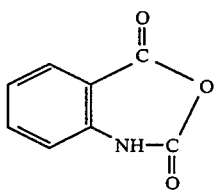

and said mono primary amine reactant is either:
(i) a hydrocarbyl mono primary amine of the formula

in which R is a monovalent straight-chained or branched-chained hydrocarbyl radical having from about 6 to about 22 carbon atoms or a hydrocarbyl aminoalkylene radical in which the hydrocarbyl group has from about 6 to about 22 carbon atoms and in which the divalent alkylene group has from about 2 to 3 carbon atoms; or
(ii) a hydrocarbon-substituted mono primary ether amine of the formula

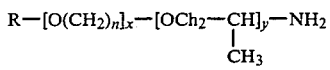

in which R is as previously described, x is an integer with a value of 0 or 1, y has a value from 0 to 10, and n is an integer from 1 to 5; and
(b) thereafter further reacting at an elevated temperature said intermediate reaction product with a substantially equimolar amount of a nitrogen-containing compound which may be either:
(i) a heterocyclic azole compound selected from the group consisting of tolyltriazole, benzotriazole, aminotriazole, aminotetrazole, aminomercaptothiadiazole, and benzomercaptothiazole; or
(ii) a polyalkylene polyamine compound of the formula

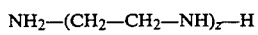

in which z is an integer from 1 to 5.

2. The lubricating oil composition of claim 1, comprising from about 0.5 to 2.0 weight percent of said reaction product.

3. The lubricating oil composition of claim 1, where said dibasic acid anhydride reactant is selected from the group consisting of maleic anhydride, alpha-methyl maleic anhydride, alpha-ethyl maleic anhydride, and alpha, beta-dimethyl maleic anhydride.

4. The lubricating oil composition of claim 3, where said dibasic acid anhydride reactant is maleic anhydride.

5. The lubricating oil composition of claim 1, where said isatoic anhydride reactant is a substituted isatoic anhydride bearing inert hydrocarbyl substituents selected from the group consisting of alkyl, aralkyl, alkaryl, aryl, or cycloalkyl hydrocarbyl substituents, or mixtures thereof.

6. The lubricating oil composition of claim 1, where R in said hydrocarbon-substituted mono primary amine reactant is an aliphatic radical having from about 10 to 18 carbon atoms.

7. The lubricating oil composition of claim 1, where said hydrocarbon-substituted mono primary amine reactant is a t-alkyl primary amine having from about 8 to 22 carbon atoms.

8. The lubricating oil composition of claim 1, where R in said hydrocarbon-substituted mono primary ether amine reactant is an aliphatic radical having from 10 to 18 carbon atoms, y is 0, x is 1, and n has a value of 2 or 3.

9. The lubricating oil composition of claim 8, in which R is an aliphatic radical having from 10 to 13 carbon atoms, y is 0, x is 1, and n is 3.

10. The lubricating oil composition of claim 1, where R in said hydrocarbon-substituted mono primary ether amine reactant is an aliphatic radical having from 10 to 18 carbon atoms, x is 0, and y has a value from 1 to 5.

11. The lubricating oil composition of claim 10, in which R is an aliphatic radical having from 10 to 13 carbon atoms, x is 0, and y is 2.

12. The lubricating oil composition of claim 1, wherein said intermediate reaction product is further reacted at an elevated temperature with a substantially equimolar amount of tolyltriazole.

13. The lubricating oil composition of claim 1, wherein said intermediate reaction product is further reacted at an elevated temperature with a substantially equimolar amount of benzotriazole.

14. The lubricating oil composition of claim 1, wherein said intermediate reaction product is further reacted at an elevated temperature with a substantially equimolar amount of aminotriazole.

15. The lubricating oil composition of claim 14, wherein said aminotriazole is selected from the group consisting of 3-, 4-, and 5-aminotriazole.

16. The lubricating oil composition of claim 1, wherein said intermediate reaction product is further reacted at an elevated temperature with a substantially equimolar amount of aminotetrazole.

17. The lubricating oil composition of claim 16, wherein said aminotetrazole is selected from the group consisting of 4- and 5-aminotetrazole.

18. The lubricating oil composition of claim 1, wherein said intermediate reaction product is further reacted at an elevated temperature with a substantially equimolar amount of aminomercaptothiadiazole.

19. The lubricating oil composition of claim 18, wherein said aminomercaptothiadiazol is 5-amino-2-mercapto-1,3,4 thiadiazole.

20. The lubricating oil composition of claim 1, wherein said intermediate reaction product is further reacted at an elevated temperature with a substantially equimolar amount of benzomecaptothiazole.

21. The lubricating oil composition of claim 1, wherein said intermediate reaction product is further reacted at an elevated temperature with a substantially equimolar amount of a polyalkylene polyamine of the formula:

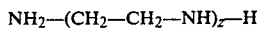

in which z is an integer with a value of 1-3.

22. The lubricating oil of claim 21, wherein said intermediate reaction product is further reacted at an elevated temperature with a substantially equimolar amount of ethylene diamine.

23. The lubricating oil of claim 21, wherein said intermediate reaction product is further reacted at an elevated temperature with a substantially equimolar amount of diethylene triamine.

24. The lubricating oil of claim 21, wherein said intermediate reaction product is further reacted at an elevated temperature with a substantially equimolar amount of triethylene tetramine.

25. The method of preparing a lubricating oil composition characterized by its corrosion, oxidation, rust-inhibiting, and haze resistance properties, suitable for use in a marine diesel engine crankcase, which comprises adding to a major portion of a hydrocarbon lubricating oil, suitable for use as lubricant in the crankcase of a marine diesel engine, a minor effective amount of 0.1-5.0 wt. % of a reaction product prepared by:

(a) first reacting at a temperature ranging from 50° to 150° C. substantially equimolar amounts of an anhydride compound and a hydrocarbon-substituted mono primary amine to produce an intermediate reaction product, where said dibasic acid anhydride reactant is either a dibasic acid anhydride of the formula

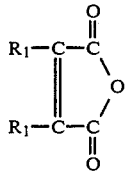

where $R_1$ is H, $CH_3$, or $C_2H_5$, or isatoic anhydride of the formula

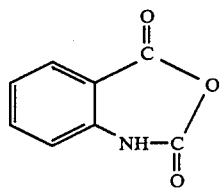

and said mono primary amine reactant is either:
(i) a hydrocarbyl mono primary amine of the formula

in which R is a monovalent straight-chained or branched-chained hydrocarbyl radical having from about 6 to about 22 carbon atoms or a hydrocarbyl aminoalkylene radical in which the hydrocarbyl group has from about 6 to about 22 carbon atoms and in which the divalent alkylene group has from about 2 to 3 carbon atoms; or
(ii) a hydrocarbon-substituted mono primary ether amine of the formula

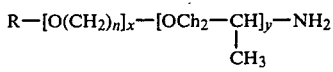

in which R is as previously described, x is an integer with a value of 0 or 1, y has a value from 0 to 10, and n is an integer from 1 to 5; and (b) thereafter further reacting at an elevated temperature said intermediate reaction product with a substantially equimolar amount of a nitrogen-containing compound which may be either:
(i) a heterocyclic azole compound selected from the group consisting of tolyltriazole, benzotriazole, aminotriazole, aminotetrazole, aminomercaptothiadiazole, and benzomercaptothiazole; or
(ii) a polyalkylene polyamine compound of the formula

in which z is an integer from 1 to 5.

26. The method of preparing a lubricating oil composition characterized by its corrosion, oxidation, rust-inhibiting, and haze resistance properties, suitable for use in a railway diesel engine crankcase, which comprises adding to a major portion of a hydrocarbon lubricating oil, suitable for use as lubricant in the crankcase of a railway diesel engine, a minor effective amount of 0.1-5.0 wt. % of a reaction product prepared by:

(a) first reacting at a temperature ranging from 50° to 150° C. substantially equimolar amounts of an anhydride compound and a hydrocarbon-substituted mono primary amine to produce an intermediate reaction product, where said anhydride reactant is either a dibasic acid anhydride of the formula

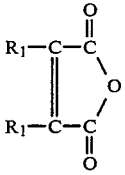

where $R_1$ is H, $CH_3$, or $C_2H_5$, or isatoic anhydride of the formula

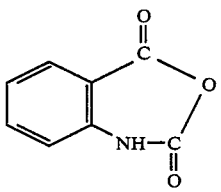

and said mono primary amine reactant is either:

(i) a hydrocarbyl mono primary amine of the formula

R—NH$_2$ in which R is a monovalent straight-chained or branched-chained hydrocarbyl radical having from about 6 to about 22 carbon atoms or a hydrocarbyl aminoalkylene radical in which the hydrocarbyl group has from about 6 to about 22 carbon atoms and in which the divalent alkylene group has from about 2 to 3 carbon atoms; or (ii) a hydrocarbon-substituted mono primary ether amine of the formula $$R-[O(CH_2)_n]_x-[OCh_2-\underset{\underset{CH_3}{|}}{CH}]_y-NH_2$$

in which R is as previously described, x is an integer with a value of 0 or 1, y has a value from 0 to 10, and n is an integer from 1 to 5; and (b) thereafter further reacting at an elevated temperature said intermediate reaction product with a substantially equimolar amount of a nitrogen-containing compound which may be either:
  (i) a heterocyclic azole compound selected from the group consisting of tolyltriazole, benzotriazole, aminotriazole, aminotetrazole, aminomercaptothiadiazole, and benzomercaptothiazole; or
  (ii) a polyalkylene polyamine compound of the formula NH$_2$—(CH$_2$—CH$_2$—NH)$_z$—H in which z is an integer from 1 to 5.

* * * * *

UNITED STATES PATENT AND TRADEMARK OFFICE
CERTIFICATE OF CORRECTION

PATENT NO. : 4,705,642

DATED : November 10, 1987

INVENTOR(S) : Rodney L. Sung; Benjamin H. Zoleski; Ronald L. O'Rourke.

It is certified that error appears in the above—identified patent and that said Letters Patent is hereby corrected as shown below:

In Claim 19, Column 19, line 2 of the Patent, change "aminomercaptothiadiazol" to --aminomercaptothiadiazole--.

In Claim 25, Column 20, line 13 of the Patent, change the formula "$R-[O(CH_2)_n]_x - [OCh_2-\underset{CH_3}{\overset{|}{CH}}]_y-NH_2$"

to --$R-[O(CH_2)_n]_x - [OCH_2-\underset{CH_3}{\overset{|}{CH}}]_y-NH_2$--.

UNITED STATES PATENT AND TRADEMARK OFFICE
CERTIFICATE OF CORRECTION

PATENT NO. : 4,705,642

DATED : November 10, 1987

INVENTOR(S) : Rodney L. Sung; Benjamin H. Zoleski; Ronald L. O'Rourke.

It is certified that error appears in the above-identified patent and that said Letters Patent is hereby corrected as shown below:

In Claim 26, Column 22, line 2 of the Patent, change the formula "$R-[O(CH_2)_n]_x - [OCh_2-\underset{\underset{CH_3}{|}}{CH}]_y-NH_2$"

to $--R-[O(CH_2)_n]_x - [OCH_2-\underset{\underset{CH_3}{|}}{CH}]_y-NH_2--$.

Signed and Sealed this

Twenty-third Day of August, 1988

Attest:

DONALD J. QUIGG

*Attesting Officer*   *Commissioner of Patents and Trademarks*